(12) United States Patent
Hwang

(10) Patent No.: US 9,944,684 B2
(45) Date of Patent: Apr. 17, 2018

(54) CETP ANTIGENIC PEPTIDE AND FUSION PROTEIN AND THEIR COMPOSITION AND APPLICATIONS

(71) Applicant: Taipei Medical University, Taipei (TW)

(72) Inventor: Jaulang Hwang, Taipei (TW)

(73) Assignee: Taipei Medical University, Taipei (TW)

( * ) Notice: Subject to any disclaimer, the term of this patent is extended or adjusted under 35 U.S.C. 154(b) by 0 days.

(21) Appl. No.: 14/920,283

(22) Filed: Oct. 22, 2015

(65) Prior Publication Data

US 2016/0145312 A1 May 26, 2016

Related U.S. Application Data

(60) Provisional application No. 62/066,910, filed on Oct. 22, 2014.

(51) Int. Cl.

| | | |
|---|---|---|
| *C07K 14/47* | (2006.01) |
| *C07K 16/18* | (2006.01) |
| *A61K 39/00* | (2006.01) |
| *A61K 45/06* | (2006.01) |
| *A61K 38/00* | (2006.01) |

(52) U.S. Cl.
CPC .......... *C07K 14/47* (2013.01); *A61K 39/0005* (2013.01); *A61K 45/06* (2013.01); *C07K 16/18* (2013.01); *A61K 38/00* (2013.01); *C07K 2317/21* (2013.01); *C07K 2317/24* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,284,533 B1 | 9/2001 | Thomas | |
| 6,410,022 B1 * | 6/2002 | Rittershaus | A61K 39/0012 424/185.1 |
| 7,074,407 B1 | 7/2006 | Kwoh et al. | |
| 7,750,123 B2 * | 7/2010 | Marasco | C07K 16/10 424/130.1 |
| 2004/0197314 A1 * | 10/2004 | Delcayre | A61K 47/48246 424/93.21 |
| 2009/0104211 A1 | 4/2009 | Szperka et al. | |
| 2015/0328296 A1 | 11/2015 | Oliva et al. | |

FOREIGN PATENT DOCUMENTS

WO    2014/003531 A1    1/2014

OTHER PUBLICATIONS

Swenson et al. Mechanism of Cholesteryl Ester Transfer Protein inhibition by a neutralizing monoclonal antibody and mapping of the monoclonal antibody epitope. J. Biol. Chem. 264, 14318-14326, 1989.*
Gaofu et al. Long-lasting specific antibodies against CETP induced by subcutaneous and mucosal administration of a 26-amino acid CETP epitope carried by heat shock protein 65 kDa in the absence of adjuvants. Vaccine, 22, 3187-3194, 2004.*
Yi et al., Improved efficacy of DNA vaccination against breast cancer by boosting with the repeat beta-hCG C-terminal peptide carried by mycobacterial heat-shock protein HSP65, Vaccine 24, 2575-2584, 2006.*
Hsu et al. (2000) "Vaccination against Gonadotropin-releasing Hormone (GnRH) Using Toxin Receptor-binding Domain-conjugated GnRH Repeats," Cancer Res. 60(14)3701-3705.
Li (2009) "Cholesteryl Ester Transfer Protein (CETP) is an Important Regulator to Affect Fatty Liver in CETP Transgenic Mice," Masters Thesis, Institute of Biochemistry and Biotechnology, Chung Shan Medical University—English abstract only.
Ota et al. (2006) "A Fusion Protein of IgG Fc and Mouse-Derived Antigen on the Surface of Pseudorabies Virus Particles Does Not Accelerate Production of Harmful Auto-Reactive Antibodies," J. Vet Med. Sci. 68(11):1179-1183.
Ritterhaus et al. (2000) "Vaccine-Induced Antibodies Inhibit CETP Activity In Vivo and Reduce Aortic Lesions in a Rabbit Model of Atherosclerosis," Vasc. Biol. 20(9):2106-2112.
Saito et al. (1999) "Epitope mapping for the anti-rabbit cholesteryl ester transfer protein monoclonal antibody that selectively inhibits triglyceride transfer," J. Lipid. Res. 40(11)2013-2021.

\* cited by examiner

*Primary Examiner* — Elly-Gerald Stoica
(74) *Attorney, Agent, or Firm* — WPAT, P.C., Intellectual Property Attorneys; Anthony King

(57) ABSTRACT

The disclosure provides an antigenic peptide targeting the extracellular, but not the intracellular, form of CETP to reduce the level of LDL (including oxLDL and other derivatives of LDL) and increase the level of HDL. Accordingly, the disclosure provides a CETP vaccine to overcome the low immunogenicity of CETP and for long-term inhibition of CETP activity to prevent or treat oxLDL or other LDL derivative-related diseases/symptoms.

9 Claims, 8 Drawing Sheets

CETP ANTIGENIC PEPTIDE AND FUSION PROTEIN AND THEIR COMPOSITION AND APPLICATIONS

RELATED APPLICATIONS

This application claims priority to U.S. Provisional Application Ser. No. 62/066,910, filed Oct. 22, 2014, the content of which is incorporated herein by reference in its entirety.

FIELD

The invention relates to an antigenic peptide for selective inhibition of plasma, but not cellular, cholesteryl ester transport protein (CETP), a fusion protein comprising the antigenic peptide and a method for eliciting a CETP antibody to reduce the level of LDL and increase the level of HDL. Particularly, the antigenic peptide is a B cell epitope derived from CETP.

BACKGROUND

HDL continues to attract interest because its level is inversely associated with the risk of cardiovascular disease. This may be attributed to its various potentially anti-atherogenic properties, such as reverse cholesterol transport, anti-inflammatory, anti-oxidative, and anti-thrombotic effects. Clinical studies have shown that low HDL-C is also found in non-alcoholic steatohepatitis (NASH). NASH shares several characteristics with atherosclerosis, including lipid accumulation, inflammation, and macrophage infiltration. The pathogenesis of NASH involves scavenger receptor-mediated uptake of ox-LDL by macrophages in the liver.

Cholesteryl ester transfer protein (CETP) is considered a therapeutic target for increasing HDL-C. Interest in CETP as a therapeutic target began as a result of the high HDL-C and low LDL-C observed in Japanese people carrying the homozygous, defective CETP gene who showed no evidence of premature atherosclerosis, even though they had hypercholesterolemia. This CETP is bound mainly to HDL particles and transfers cholesterol ester from HDL to triglyceride-rich lipoproteins. CETP action results in a CE enrichment of non-HDL lipoproteins, which could contribute to atherosclerosis. Small molecule CETP inhibitors, including dalcetrapib, evacetrapib, and anacetrapib that are at various phases of clinical development inhibit CETP activity and significantly increase HDL-C. However, torcetrapib failed in phase 3 clinical trials due to compound specific off-target effects, and dalcetrapib failed in phase 3 clinical trials due to less meaningful outcomes. Two other CETP inhibitors, evacetrapib and anacetrapib, are still under clinical trials. Inducing an immune response against specific self-peptides is potentially beneficial for the treatment of certain diseases. The drawbacks of peptide-based immunization include low immunogenicity of self-peptides, a low efficiency of chemical conjugation, and the heterogeneous nature of antigen preparations.

U.S. Pat. No. 7,074,407 B1 provides a method for increasing HDL cholesterol in a mammal by stimulating an immune response that inhibits the function of CETP. U.S. Pat. No. 6,284,533 B1 provides a plasmid-based vaccine based on the combination of DNA segments coding for one or more B cell epitopes of cholesteryl ester transfer protein (CETP) and one or more broad range helper T cell epitopes. US20090104211 provides a CETP mimotope which, in their amino acid sequence are completely different from the amino acid sequence of CETP or of fragments of CETP. U.S. Pat. No. 6,410,022 B1 relates to peptides comprising a helper T cell epitope portion and a B cell epitope portion for eliciting an immune response against endogenous cholesteryl ester transfer protein (CETP) activity to prevent or treat cardiovascular disease, such as atherosclerosis. WO2014003531 provides a novel vaccine composition of micellar nanoparticles consisting of carboxyl terminal of CETP peptide immunogen for intranasal administration for the treatment and/or prevention of atherosclerosis disease or non-alcoholic fatty liver resulting from an abnormal metabolism of circulating lipids. Although a number of antigens are developed, their immunogenicity and efficiency are not sufficient.

Therefore, there is still a need to develop a CETP peptide immunogen having advantageous immunogenicity.

SUMMARY

This disclosure relates to the generation of therapeutics that selectively inhibit the action of plasma CETP to result in health benefits by reducing the level of LDL (including oxLDL and other derivatives of LDL) and increasing the level of HDL. One of the therapeutic compositions is an effective vaccine, in which at least five identical B cell epitopes are arranged as tandem repeats for activation of B cells. The disclosure also relates to the polyvalent antigen as a tandem repeat structure and its use for developing vaccines against CETP for health benefits.

The disclosure provides an isolated antigenic peptide for eliciting a CETP antibody, comprising at least one repeat of an amino acid sequence consisting of PEHLLVDFLQSL (SEQ ID NO:1) or a modified peptide thereof for eliciting a CETP antibody. The embodiments of the isolated antigenic peptide include but are not limited to those comprising at least two, three, four or five repeats of the amino acid sequence of SEQ ID NO:1 or a modified peptide thereof for eliciting a CETP antibody, and those comprising 2 to 10 repeats or a modified peptide thereof for eliciting a CETP antibody, that comprising 4 to 8 repeats or a modified peptide thereof for eliciting a CETP antibody. Preferably, the isolated antigenic peptide comprises 5 to 7 repeats or a modified peptide thereof for eliciting a CETP antibody. More preferably, the isolated antigenic peptide comprises 6 repeats or a modified peptide thereof for eliciting a CETP antibody.

The disclosure also provides an antigenic fusion protein for eliciting a CETP antibody, comprising an antigenic fusion protein comprising an antigenic peptide of the disclosure fused to a domain for increasing uptake by antigen presenting cells (APC), or a modified protein thereof for eliciting a CETP antibody. In some embodiments, the domain for increasing uptake by antigen presenting cells (APC) is selected from the group including Fc fragment of IgGs, Fc fragment of IgM, and Fc fragment of IgA. Preferably, the domain is Fc fragment of IgG. More preferably, the domain is an Fc fragment of human or rabbit IgG.

The disclosure also provides a therapeutic agent for reducing the level of LDL (including oxLDL and other derivatives of LDL) and increasing the level of HDL through selective inhibition of plasma, but not cellular CETP. In one embodiment, the therapeutic agent is an antibody binding to the isolated antigenic peptide or antigenic fusion protein of the disclosure. In some embodiments, the antibody is a polyclonal antibody, monoclonal antibody, chimeric antibody, humanized antibody or human antibody.

The disclosure further provides a pharmaceutical agent or composition, comprising the isolated antigenic peptide or an antigenic fusion protein or an antibody of the disclosure. In one embodiment, the pharmaceutical agent or composition is a vaccine composition.

The disclosure further provides a method for eliciting or activating a CETP antibody in a subject, comprising administering an effective amount of an isolated antigenic peptide or an antigenic fusion protein of the disclosure to the subject. The elicited CETP antibody targets the extracellular, but not the intracellular, form of CETP to reduce the level of LDL (including oxLDL and other derivatives of LDL) and increase the level of HDL. On the other hand, the disclosure provides a use of an isolated antigenic peptide or an antigenic fusion protein or an antibody of the disclosure in the manufacture of a medicament for eliciting or activating a CETP antibody in a subject.

In one embodiment, the disclosure provides a method for reducing the level of LDL and increasing the level of HDL in a subject, comprising administering an effective amount of an isolated antigenic peptide or an antigenic fusion protein or an antibody of the disclosure to the subject. Accordingly, the disclosure provides a method for treating or preventing an oxLDL or LDL derivative-related disease, comprising administering an effective amount of an isolated antigenic peptide or an antigenic fusion protein or an antibody of the disclosure to the subject. On the other hand, the disclosure provides a use of an isolated antigenic peptide or an antigenic fusion protein or an antibody of the disclosure in the manufacture of a medicament for reducing the level of LDL and increasing the level of HDL in a subject. In addition, the disclosure provides a use of an isolated antigenic peptide or an antigenic fusion protein or an antibody of the disclosure in the manufacture of a medicament for treating or preventing an oxLDL or LDL derivative-related disease in a subject.

BRIEF DESCRIPTION OF THE DRAWING

(FIG. 1A) Schematic diagram of Fc-CETP6. (FIG. 1B) The products of adapter-PCR. (FIG. 1C) Purity of the His-tagged Fc-CETP6 immunogen.

(FIG. 2A) Plasma antibody titers against CETP. (FIG. 2B) Plasma CETP activity.

(FIG. 3A) Representative Sudan IV-stained aortic specimens at the end of week 24. (FIG. 3B) Quantification of the aortic lesion area. (FIG. 3C) Expression of NF-κB and RAM-1 1 (magnification, ×200) of the aorta from normal rabbits, control rabbits, and Fc-CETP6 rabbits. (FIG. 3D) Quantification of the RAM-11 and (FIG. 3E) NF-κB positive area of aorta.

(FIG. 4A), (FIG. 4B) Representative liver sections stained with H&E (magnification, ×200). (FIG. 4C) Expression of RAM-11 (magnification, upper panel ×100 and lower panel ×400) of the liver from control and Fc-CETP6 rabbits. (FIG. 4D) Expression of NF-κB (magnification, upper panel ×100 and lower panel ×400) of the liver from control and Fc-CETP6 rabbits. (FIG. 4E) Expression of inflammation related genes in control rabbits (black bars) and Fc-CETP6 rabbits (white bars).

(FIG. 5A) Representative liver sections stained with Masson's trichrome stain and immunohistochemistry stained for α-SMA, a marker of activated stellate cells and myofibroblasts. (FIG. 5B) Expression of fibrosis related genes in control rabbits (black bars) and Fc-CETP6 rabbits (white bars).

DETAILED DESCRIPTION

Figure 1A:
FIGS. 1A-C show the preparation of the Fc-CETP6 vaccine.

The disclosure is based, at least inpart, on an antigenic peptide targeting the extracellular, but not the intracellular, form of CETP, to reduce the level of LDL (including oxLDL and other derivatives of LDL) and increase the level of HDL. Accordingly, the disclosure provides a CETP vaccine to overcome the low immunogenicity of CETP and for long-term inhibition of CETP activity to prevent or treat oxLDL or other LDL derivative-related diseases/symptoms.

Definitions

In the description that follows, a number of terms are used and the following definitions are provided to facilitate understanding of the claimed subject matter. Terms that are not expressly defined herein are used in accordance with their plain and ordinary meanings.

It should be noted that, as used in this specification and the appended claims, the singular forms "a," "an" and "the" include plural referents unless the content clearly dictates otherwise. Thus, for example, reference to "a peptide" includes a mixture of two or more such peptides, and the like.

As used herein, the use of "or" means "and/or" unless stated otherwise. In the context of a multiple dependent claim, the use of "or" refers back to more than one preceding independent or dependent claim in the alternative only.

It is noted that in this disclosure and particularly in the claims and/or paragraphs, terms such as "comprises," "comprised," "comprising" and the like can mean "includes," "included," "including," and the like; and that terms such as "consisting essentially of" and "consists essentially of" allow for elements not explicitly recited, but exclude elements that are found in the prior art or that affect a basic or novel characteristic of the disclosure.

As used herein, the term "isolated," when referring to a polypeptide, means that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

As used herein, the term "antigen" refers to a molecule, such as a protein, polypeptide, or fragment thereof, containing an epitope(s) (either linear, conformational or both) that will stimulate a host's immune system to make a humoral and/or cellular antigen-specific response. The term is used interchangeably with the term "immunogen." Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in DNA immunization applications, is also included in the definition of antigen herein.

As used herein, the term "epitope" generally refers to the site on an antigen which is recognized by a T-cell receptor and/or an antibody. Preferably it is a short peptide derived from or as part of a protein antigen. Several different epitopes may be carried by a single antigenic molecule. The term "epitope" also includes modified sequences of amino acids that stimulate responses which recognize the whole organism.

As used herein, the "immunogenic" protein, polypeptide or peptide means a molecule that includes one or more epitopes and thus can modulate an immune response. Such peptides can be identified using any number of epitope mapping techniques, well known in the art, e.g., Epitope Mapping Protocols in Methods in Molecular Biology, Vol. 66 (Glenn E. Morris, Ed., 1996) Humana Press, Totowa, N.J.

As used herein, the "immunological response" to a composition or vaccine is the development in the host of a cellular and/or antibody-mediated immune response to a composition or vaccine of interest. Usually, an "immunological response" includes, but is not limited to, one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

As used herein, the term "peptide" refers to a polymeric molecule having amino acid residues which are linked to each other by peptide bonds.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for the purposes of the present disclosure, a "polypeptide" refers to a protein which includes modifications, such as deletions, additions and substitutions, to the native sequence, so long as the protein maintains the desired activity. These modifications may be deliberate, as through site-directed mutagenesis, or may be accidental, such as through mutations of hosts which produce the proteins or errors due to PCR amplification.

As used herein, the term "vaccine" is used interchangeably with "immunoprotective composition" and refers to an immunogen that, upon inoculation into a host organism, can induce complete or partial immunity to pathogenic agents, or can reduce the effects of diseases associated with pathogenic agents.

As used herein, the terms "condition," "disease," "symptoms," and "disorder" are used interchangeably.

The terms "administer," "administering," or "administration," as used herein, refers to absorbing, ingesting, injecting, inhaling, or otherwise introducing an inventive agent, or a pharmaceutical composition thereof, in or on a subject.

As used herein, "therapeutically effective amount" means an amount of an immunogen/antigen/epitope what will induce an immunological response.

As used herein, the terms "prevent," "preventing" and "prevention" refer to the prevention of the onset, recurrence or spread of a disease or disorder, or of one or more symptoms thereof. In certain embodiments, the terms refer to the treatment with or administration of an antigen or a protein or an antibody, with or without one or more other additional active agents, prior to the onset of symptoms, particularly to patients at risk of disease or disorders provided herein. The terms encompass the inhibition or reduction of a symptom of the particular disease. In this regard, the term "prevention" may be interchangeably used with the term "prophylactic treatment."

As used herein, the term "subject" is defined to include animals such as mammals, including, but not limited to, primates (e.g., humans), cows, sheep, goats, horses, dogs, cats, rabbits, rats, mice and the like. In specific embodiments, the subject is a human. The terms "subject" and "patient" are used interchangeably herein in reference, for example, to a mammalian subject, such as a human.

Further, the contents of all cited references (including literature references, patents, patent applications, and websites) that maybe cited throughout this application are hereby expressly incorporated by reference in their entirety for any purpose, as are the references cited therein.

Antigenic Peptides and Antigenic Fusion Protein

In one aspect, the disclosure provides an isolated antigenic peptide for eliciting a CETP antibody, comprising at least one repeat of an amino acid sequence consisting of PEHLLVDFLQSL (SEQ ID NO:1) or a modified peptide thereof for eliciting a CETP antibody.

In one embodiment, the isolated antigenic peptide comprises at least two, three, four or five repeats of the amino acid sequence of SEQ ID NO:1 or a modified peptide thereof for eliciting a CETP antibody. In some embodiments, the isolated antigenic peptide comprises 2 to 10 repeats or a modified peptide thereof for eliciting a CETP antibody. In a further embodiment, the isolated antigenic peptide comprises 4 to 8 repeats or a modified peptide thereof for eliciting a CETP antibody. Preferably, the isolated antigenic peptide comprises 5 to 7 repeats or a modified peptide thereof for eliciting a CETP antibody. More preferably, the isolated antigenic peptide comprises 6 repeats or a modified peptide thereof for eliciting a CETP antibody.

In another aspect, the disclosure provides an antigenic fusion protein for eliciting a CETP antibody, comprising an antigenic peptide of the disclosure fused to a domain for increasing uptake by antigen presenting cells (APC) or a modified protein thereof for eliciting a CETP antibody. In some embodiments, the domain for increasing uptake by antigen presenting cells (APC) is selected from the group including Fc fragment of IgGs, Fc fragment of IgM, and Fc fragment of IgA. In a further embodiment, the domain is Fc fragment of IgG. Preferably, the domain is an Fc fragment of human or rabbit IgG.

```
Polynulcotide sequence of Fc fragment of
human IgG (SEQ ID NO: 2):
atggcacctgaactcctgggggggaccgtcagtcttcctcttcccc ccaaaacccaaggacaccctcatgatctcccggacccctgaggtc acatgcgtggtggtggacgtgagccacgaagaccctgaggtcaag ttcaactggtacgtggacggcgtggaggtgcataatgccaagaca aagccgcgggaggagcagtacaacagcacgtaccgtgtggtcagc gtcctcaccgtcctgcaccaggactggctgaatggcaaggagtac aagtgcaaggtctccaacaaagccctcccagccccccatcgagaaa accatctccaaagccaaagggcagccccgagaaccacaggtgtac
```

```
accctgccccatcccgggatgagctgaccaagaaccaggtcagc ctgacctgcctggtcaaaggcttctatcccagcgacatcgccgtg gagtgggagagcaatgggcagccggagaacaactacaagaccacg cctcccgtgctggactccgacggctccttcttcctctacagcaag ctcaccgtggacaagagcaggtggcagcaggggaacgtcttctca tgctccgtgatgcatgaggctctgcacaaccactacacgcagaag agcctctccctgtctccgggtaaaggatccccttgttgtggatgc tgcggttgcggatgcccttgttgtggatgctgcggttgcggatgc ccttgttgtggatgctgcggttgcggatgcccttgttgtggatgc tgcggttgcggatgcccttgttgtggatgctgcggttgcggatgc ccttgttgtggatgctgcggttgcggatgcccttgttgtggatgc tgcggttgcggatgcaagcttcatcaccaccatcaccatgagctt catcatcatcatcatcattaa Polypeptide sequence of Fc fragment of
human IgG (SEQ ID NO: 3):
M A P E L L G G P S V F L F P P K P K D T L M

I S R T P E V T C V V V D V S H E D P E V K F

N W Y V D G V E V H N A K T K P R E E Q Y N S

T Y R V V S V L T V L H Q D W L N G K E Y K C

K V S N K A L P A P I E K T I S K A K G Q P R

E P Q V Y T L P P S R D E L T K N Q V S L T C

L V K G F Y P S D I A V E W E S N G Q P E N N

Y K T T P P V L D S D G S F F L Y S K L T V D

K S R W Q Q G N V F S C S V M H E A L H N H Y

T Q K S L S L S P G K G S P C C G C C G C G C

P C C G C C G C G C P C C G C C G C G C P C C

G C C G C G C P C C G C C G C G C P C C G C C

G C G C P C C G C C G C G C K L H H H H H H E

L H H H H H H stop

Polynulcotide sequence of Fc fragment of
rabbit IgG (SEQ ID NO: 4)
gcccctcgacaagc agcaagcccacgt gcccacccc tgaactcctg gggggaccgt ctgtcttcat cttcccccaaaacccaagg acaccctcat gatctcacgc accccgagg tcacatgcgt ggtggtggacgtgagccagg atgacccga ggtgcagttc acatggtaca taaacaacga gcaggtgcgcaccgcccggc cgccgctacg ggagcagcag ttcaacagca cgatccgcgt ggtcagcaccctcccatca cgcaccagga ctggctgagg ggcaaggagt tcaagtgcaa agtccacaac cgagaaaacc atctccaaag ccagagggca gccccctggagccgaaggtct acaccatggg ccctccccgg gaggagctga gcagcaggtc ggtcagcctgacctgcatga tcaacggctt ctaccccttcc gacatctcgg tggagtggga
```

```
gaagaacgggaaggcagagg acaactacaa gaccacgccg gccgtgctgg acagcgacgg ctcctacttcctctacaaca agctctcagt gcccacgagt gagtggcagc ggggcgacgt cttcacctgctccgtgatgc acgaggcctt gcacaaccac tacacgcaga agtccatctc ccgctctccgggtaaa
```

Polypeptide sequence of Fc fragment of
rabbit IgG (SEQ ID NO: 5):
A P S T S S K P T C P P P E L L G G P S V F I

F P P K P K D T L M I S R T P E V T C V V V D

V S Q D D P E V Q F T W Y I N N E Q V R T A R

P P L R E Q Q F N S T I R V V S T L P I T H Q

D W L R G K E F K C K V H N K A L P A P I E K

T I S K A R G Q P L E P K V Y T M G P P R E E

L S S R S V S L T C M I N G F Y P S D I S V E

W E K N G K A E D N Y K T T P A V L D S D G S

Y F L Y N K L S V P T S E W Q R G D V F T C S

V M H E A L H N H Y T Q K S I S R S P G K G S

P C C G C C G C G C P C C G C C G C G C P C C

G C C G C G C P C C G C C G C G C P C C G C C

G C G C P C C G C C G C G C P C C G C C G C G

C K L R S G H H H H H H G R S G H H H H H H G

In some embodiments, the antigenic fusion protein comprises a Fc fragment fused to a linear repeat comprising at least two, three, four or five amino acid sequences of SEQ ID NO:1, or a modified protein thereof for eliciting a CETP antibody. In some embodiments, the antigenic fusion protein comprises a Fc fragment fused to a linear repeat comprising 2 to 10 amino acid sequences of SEQ ID NO:1, or a modified protein thereof for eliciting a CETP antibody. In a further embodiment, the antigenic fusion protein comprises a Fc fragment fused to a linear repeat comprising 4 to 8 amino acid sequences of SEQ ID NO:1, or a modified protein thereof for eliciting a CETP antibody. Preferably, antigenic fusion protein comprises a Fc fragment fused to a linear repeat comprising 5 to 7 amino acid sequences of SEQ ID NO:1, or a modified protein thereof for eliciting a CETP antibody. More preferably, the antigenic fusion protein comprises an Fc fragment fused to a linear repeat comprising 6 amino acid sequences of SEQ ID NO:1 (Fc-CETP$_6$), or a modified protein thereof for eliciting a CETP antibody. In some embodiments, the antigenic fusion protein comprises an Fc fragment of rabbit IgG fused to a linear repeat comprising 6 amino acid sequences of SEQ ID NO:1 (rFc-CETP$_6$) or an Fc fragment of human IgG fused to a linear repeat comprising 6 amino acid sequences of SEQ ID NO:1 (hFc-CETP$_6$). The polynucleotide sequences of rFc-CETP$_6$ and hFc-CETP$_6$ are described below.

```
Polynulcotide sequence of hFc-CETP6
                          (SEQ ID NO: 6)
CATATGGCACCTGAACTCCTGGGGGGACCGTCAGTCTTCCTCTTC

CCCCCAAAACCCAAGGACACCCTCATGATCTCCCGGACCCCTGAG
```

-continued
GTCACATGCGTGGTGGTGGACGTGAGCCACGAAGACCCTGAGGTC

AAGTTCAACTGGTACGTGGACGGCGTGGAGGTGCATAATGCCAAG

ACAAAGCCGCGGGAGGAGCAGTACAACAGCACGTACCGTGTGGTC

AGCGTCCTCACCGTCCTGCACCAGGACTGGCTGAATGGCAAGGAG

TACAAGTGCAAGGTCTCCAACAAAGCCCTCCCAGCCCCATCGAG

AAAACCATCTCCAAAGCCAAAGGGCAGCCCCGAGAACCACAGGTG

TACACCCTGCCCCATCCCGGGATGAGCTGACCAAGAACCAGGTC

AGCCTGACCTGCCTGGTCAAAGGCTTCTATCCCAGCGACATCGCC

GTGGAGTGGGAGAGCAATGGGCAGCCGGAGAACAACTACAAGACC

ACGCCTCCCGTGCTGGACTCCGACGGCTCCTTCTTCCTCTACAGC

AAGCTCACCGTGGACAAGAGCAGGTGGCAGCAGGGGAACGTCTTC

TCATGCTCCGTGATGCATGAGGCTCTGCACAACCACTACACGCAG

AAGAGCCTCTCCCTGTCTCCGGGTAAA GGATCC CCT TGT

TGT GGA TGC TGC GGT TGC GGA TGC CCT TGT TGT

GGA TGC TGC GGT TGC GGA TGC CCT TGT TGT GGA

TGC TGC GGT TGC GGA TGC CCT TGT TGT GGA TGC

TGC GGT TGC GGA TGC CCT TGT TGT GGA TGC TGC

GGT TGC GGA TGC CCT TGT TGT GGA TGC TGC GGT

TGC GGA TGC CCT TGT TGT GGA TGC TGC GGT TGC

GGA TGC AAGCTT AGA TCA GGT CAT CAT CAC CAC

CAT CAC GGT AGA TCA GGT CAT CAT CAC CAC CAT

CAC GGT TAA GAATTC
Bold: Restriction enzyme cutting site

Polynulcotide sequence of rFc-CETP₆
(SEQ ID NO: 7)
CATATGGCCCCTCGACAAGCAGCAAGCCCACGTGCCCACCCCT

GAACTCCTGGGGGACCGTCTGTCTTCATCTTCCCCCCAAAACCC

AAGGACACCCTCATGATCTCACGCACCCCCGAGGTCACATGCGTG

GTGGTGGACGTGAGCCAGGATGACCCCGAGGTGCAGTTCACATGG

TACATAAACAACGAGCAGGTGCGCACCGCCCGGCCGCCGCTACGG

GAGCAGCAGTTCAACAGCACGATCCGCGTGGTCAGCACCCTCCCC

ATCACGCACCAGGACTGGCTGAGGGGCAAGGAGTTCAAGTGCAAA

GTCCACAACAAGGCACTCCCGGCCCCCATCGAGAAAACCATCTCC

AAAGCCAGAGGGCAGCCCCTGGAGCCGAAGGTCTACACCATGGGC

CCTCCCCGGGAGGAGCTGAGCAGCAGGTCGGTCAGCCTGACCTGC

ATGATCAACGGCTTCTACCCTTCCGACATCTCGGTGGAGTGGGAG

AAGAACGGGAAGGCAGAGGACAACTACAAGACCACGCCGGCCGTG

CTGGACAGCGACGGCTCCTACTTCCTCTACAACAAGCTCTCAGTG

CCCACGAGTGAGTGGCAGCGGGGCGACGTCTTCACCTGCTCCGTG

ATGCACGAGGCCTTGCACAACCACTACACGCAGAAGTCCATCTCC

CGCTCTCCGGGTAAA GGATCC CCT TGT TGT GGA TGC

TGC GGT TGC GGA TGC CCT TGT TGT GGA TGC TGC

-continued
GGT TGC GGA TGC CCT TGT TGT GGA TGC TGC GGT

TGC GGA TGC CCT TGT TGT GGA TGC TGC GGT TGC

GGA TGC CCT TGT TGT GGA TGC TGC GGT TGC GGA

TGC CCT TGT TGT GGA TGC TGC GGT TGC GGA TGC

CCT TGT TGT GGA TGC TGC GGT TGC GGA TGC AAGCTT

AGA TCA GGT CAT CAT CAC CAC CAT CAC GGT AGA

TCA GGT CAT CAT CAC CAC CAT CAC GGT TAA GAATTC

Bold: Restriction Enzyme Cutting Site

Accordingly, the the antigenic fusion protein comprises the sequence encoded by SEQ ID NO:6 or SEQ ID NO:7.

Generally, it is known that modifications of one or more amino acids in a peptide do not influence the function of the peptide, or in some cases even enhance the desired function of the original protein. In fact, modified peptides (i.e., peptides consisting of an amino acid sequence modified by substituting, deleting, inserting or adding one, two or several amino acid residues to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Therefore, according to one embodiment of the present disclosure, the antigenic peptide for eliciting a CETP antibody of the present disclosure comprises at least one repeat of an amino acid sequence consisting of SEQ ID NO:1, in which one, two or even more amino acids are added, deleted, inserted and/or substituted.

One of skill in the art will recognize that individual modifications (i.e., deletions, insertions, additions or substitutions) to an amino acid sequence which alters a single amino acid or a small percentage of the overall amino acid sequence results in the conservation of the properties of the original amino acid side-chain; it is thus referred to as "conservative substitution" or "conservative modification," wherein the alteration of a protein results in a protein with similar functions. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Such conservatively modified peptides are also considered to be antigenic peptides of the present disclosure. However, the peptide of the present disclosure is not restricted thereto and may include non-conservative modifications, so long as the resulting modified peptide retains the CETP antibody elicitation of the original unmodified peptide.

The antigenic peptides or the antigenic fusion protein of the present disclosure can be prepared using well known techniques. For example, the peptides or proteins may be prepared synthetically, by recombinant DNA technology or chemical synthesis. The peptides or proteins of the present disclosure may be synthesized individually or as longer polypeptides including two or more peptides. The peptides or proteins may be isolated, i.e., purified or isolated substantially free of other naturally occurring host cell proteins and fragments thereof, or any other chemical substances.

A peptide or protein of the present disclosure may be synthesized chemically, by any of several techniques that are known to those skilled in the peptide or protein art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis, Synthesis, Biology, Vol. 1, for classical solution synthesis.

Alternatively, the present peptides or protein may be obtained adapting any known genetic engineering methods for producing peptides or proteins (e.g. recombinant expression, purification from cell culture, chemical synthesis, etc.) and in various forms (e.g. native, mutant, fusions, etc.). Means for preparing such peptides and proteins are well understood in the art. Peptides and proteins are preferably prepared in substantially pure form (i.e. substantially free from other host cell or non-host cell proteins (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the peptide or protein in an expressible form (e.g., downstream of a regulatory sequence corresponding to a promoter sequence) is prepared and transformed into a suitable host cell; such vectors and host cells are also provided by the present disclosure. The host cell is then cultured to produce the peptide or protein of interest. The peptide or protein may also be produced in vitro by adopting an in vitro translation system.

The isolated antigenic peptide or antigenic fusion protein of the disclosure is a B cell epitope derived from polypeptides of exon 9 of CETP. The isolated antigenic peptide of the disclosure can selectively block the action of plasma CETP, but not cellular CETP, and thus is more efficacious than agents that block the action of both forms of CETP. Antibodies In another aspect, the present disclosure provides a therapeutic agent for reducing the level of LDL (including oxLDL and other derivatives of LDL) and increasing the level of HDL through selective inhibition of plasma, but not cellular, CETP.

In one embodiment, the present disclosure provides an antibody binding to the isolated antigenic peptide or antigenic fusion protein of the disclosure. An antibody of the disclosure can be used in any form, such as monoclonal or polyclonal antibodies, and includes anti-serum obtained by immunizing an animal such as a rabbit with the peptide of the disclosure, all classes of polyclonal and monoclonal antibodies, human antibodies and humanized antibodies produced by genetic recombination. As used herein, an antibody is a protein that reacts with either the full length or a fragment of a CETP peptide. In a preferred embodiment, an antibody of the present disclosure recognizes fragment peptides on the exon 9 of CETP; preferably, the fragment of CETP having an amino acid sequence of SEQ ID NO:1. Methods for synthesizing oligopeptide are well known in the arts. After the synthesis, peptides may be optionally purified prior to use as immunogen. In the present disclosure, the oligopeptide may be conjugated or linked with or fused to a domain for increasing uptake by antigen presenting cells to enhance the immunogenicity. Method for conjugating the domain and peptide are also well known in the arts.

Any mammalian animal may be immunized with the antigen. In general, animals of Rodentia, Lagomorpha or Primates are used. Animals of Rodentia include, for example, mouse, rat and hamster. Animals of Lagomorpha include, for example, rabbit. Animals of Primates include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for the immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriate amount of Freund's incomplete adjuvant every 4 to 21 days. An appropriate carrier may also be used for immunization. After immunization as above, serum is examined by a standard method for an increase in the amount of desired antibodies.

Polyclonal antibodies against the peptides or proteins of the present disclosure may be prepared by collecting blood from the immunized mammal examined for the increase of desired antibodies in the serum, and by separating serum from the blood by any conventional method. Polyclonal antibodies may include serum containing the polyclonal antibodies, as well as the fraction containing the polyclonal antibodies may be isolated from the serum. Immunoglobulin G or M can be prepared from a fraction which recognizes only the peptide of the present disclosure using, for example, an affinity column coupled with the peptide of the present disclosure, and further purifying this fraction using the protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen or myeloma cells. The above immunocyte and myeloma cells can be fused according to known methods, for example, the method of Milstein et al. (Galfre and Milstein, Methods Enzymol 73: 3-46 (1981). Resulting hybridomas obtained by the cell fusion may be selected by cultivating them in a standard selection medium. Then, the standard limiting dilution is performed to screen and clone a hybridoma cell producing the desired antibody.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present disclosure also provides recombinant antibodies prepared as described above. Moreover, an antibody of the present disclosure may be a fragment of an antibody or modified antibody, so long as it binds to one or more of the peptides of the disclosure. For instance, the antibody fragment may be Fab, F(ab')2, Fv or single chain Fv (scFv), in which Fv fragments from H and L chains are ligated by an appropriate linker (Huston et al., Proc Natl Acad Sci USA 85: 5879-83 (1988)).

Alternatively, an antibody of the present disclosure may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies comprising human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991).

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto.

Pharmaceutical Agents or Compositions Containing the Peptides or Proteins or Antibodies as the Active Ingredient In another aspect, the disclosure provides a pharmaceutical agent or composition, comprising the isolated antigenic peptide or an antigenic fusion protein or an antibody of the disclosure.

The peptides or proteins or an antibody of this disclosure can be administered directly as a pharmaceutical agent or composition, or if necessary, may be formulated by conventional formulation methods. In the formulation, in addition to the peptides of this disclosure, carriers, excipients, and such that are ordinarily used for drugs can be included as appropriate without particular limitations.

The pharmaceutical agent or composition to be administered can be provided in a pharmaceutically acceptable solution such as an aqueous solution, often a saline or buffered solution, or they can be provided in powder form. There is a wide variety of suitable formulations of pharmaceutical compositions of the present disclosure (see, e.g., Lieberman, Pharmaceutical Dosage Forms, Marcel Dekker, Vols. 1-3 (1998); Remington's Pharmaceutical Science, 17th ed., Mack Publishing Company, Easton, Pa. (1985) and similar publications). Formulations suitable for oral administration can consist of (a) liquid solutions, such as an effective amount of the recombinant bacteria suspended in diluents, such as buffered water, saline or PEG 400; (b) capsules, sachets or tablets, each containing a predetermined amount of the active ingredient, as lyophilized powder, liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. It is recognized that the attenuated vaccines, when administered orally, must be protected from digestion. This is typically accomplished either by complexing the vaccines with a composition to render it resistant to acidic and enzymatic hydrolysis or by packaging the vaccines in an appropriate resistant carrier such as a liposome or enteric coated capsules. Means of protecting the attenuated bacteria from digestion are well known in the art. The pharmaceutical compositions can be encapsulated, e.g., in liposomes, or in a formulation that provides for slow release of the active ingredient.

The peptides or proteins or antibodies of this disclosure can be prepared in a combination, which includes two or more of peptides, proteins or antibodies of the present disclosure. The peptides or proteins or antibodies in the combination can be the same or different. The peptides or proteins or antibodies can be in a cocktail, or in the case of peptide or protein, the peptides or proteins of the disclosure can be conjugated to each other using standard techniques. By administering the peptides or proteins of this disclosure, the peptides or proteins are presented at a high density on APCs.

The pharmaceutical agents or compositions can be used to reduce the level of LDL (including oxLDL and other derivatives of LDL) and increase the level of HDL through selective inhibition of plasma, but not cellular, CETP, that include any peptide of this disclosure as the active ingredient. In a further embodiment, the pharmaceutical agents or compositions can additionally include an adjuvant so that cellular immunity will be established effectively, or they can be administered with other active ingredients. Examples of known suitable adjuvants include alum, aluminum phosphate, aluminum hydroxide, and MF59 (4.3% w/v squalene, 0.5% w/v Tween 80, 0.5% w/v Span 85), Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, trehalose dimycolate and cell wall skeleton (MPL+TDM+CWS) in a 2% squalene/Tween 80 emulsion, or Bacille Calmette-Guerin (BCG). The effectiveness of an adjuvant may be determined by measuring the amount of antibodies directed against the immunogenic antigen.

If necessary, the pharmaceutical agents or compositions of the present disclosure may optionally include a second active ingredient, so long as the second ingredient can reduce the level of LDL or increase the level of HDL. For example, the second active ingredient is statins (such as atorvastatin (Lipitor), fluvastatin (Lescol), lovastatin (Mevacor, Altocor), pitavastatin (Livalo), pravastatin (Pravachol), rosuvastatin (Crestor) and simvastatin (Zocor)) or niacins (such as inositol and nicotinate). The peptides or proteins of the present disclosure may also be administered sequentially or concurrently with the second active ingredient.

The amounts of the pharmaceutical agents or compositions of the present disclosure depend, for example, on what type of pharmacologic composition(s) is/are used, the disease being treated, and the scheduling and routes of administration.

Those of skill in the art will easily recognize that, in addition to the ingredients particularly mentioned herein, the pharmaceutical agents or compositions of the present disclosure may further include other substances conventional in the art having regard to the type of formulation in question (e.g., excipients, fillers, binders, diluents, etc.).

Methods of Using or Use of the Peptides, Proteins or Antibodies of the Disclosure In a further aspect, the disclosure provides a method for eliciting or activating a CETP antibody in a subject, comprising administering an effective amount of an isolated antigenic peptide or an antigenic fusion protein of the disclosure to the subject. The elicited CETP antibody targets the extracellular, but not the intracellular, form of CETP to reduce the level of LDL (including oxLDL and other derivatives of LDL) and increase the level of HDL.

In one embodiment, the disclosure provides a method for reducing the level of LDL and increasing the level of HDL in a subject, comprising administering an effective amount of an isolated antigenic peptide or an antigenic fusion protein or an antibody of the disclosure to the subject.

Accordingly, the disclosure provides a method for treating or preventing an oxLDL or LDL derivative-related disease, comprising administering an effective amount of an isolated antigenic peptide or an antigenic fusion protein or an antibody of the disclosure to the subject.

The oxLDL or LDL derivative-related diseases include but are not limited to neurodegenerative diseases, cardiovascular diseases, cholesterol metabolism-related symptoms, inflammatory diseases, liver and kidney diseases, asthma, spinal cord injury and traumatic brain injury. In some embodiments, the metabolism-related symptom is high blood pressure, fatty liver, or diabetes; the inflammatory disease is arthritis or non-alcoholic steatohepatitis (NASH); and the cardiovascular disease is stroke.

In some embodiments, the subject used in the method of the disclosure is selected from the groups including human, dog, cat, cattle, rabbits and pig.

The embodiments of the disclosure described herein selectively block the action of plasma CETP, but not cellular CETP, so it is more efficacious than agents that block the action of both forms of CETP. Thus, the embodiments described herein can reduce the level of LDL and increase the level of HDL to treat or prevent oxLDL or other LDL derivative-related diseases/symptoms.

EXAMPLES

Materials and Methods

Construction of DNA Fragment, Encoding for 6 Repeats of Human CETP Epitope, Followed by Fusing with Rabbit Fc and Expression of the Fused Protein in E. coli BL21 (DE3).

Figure 1B:
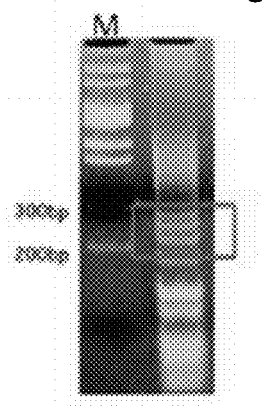

The DNA fragment encoding for 6 repeats of the peptide PEHLLVDFLQSL, a human CETP epitope (Gaofu et al. 2004, Vaccine 22: 3187-3194), was generated by the template-repeated polymerase chain reaction (TR-PCR), as described previously (Hsu et al. 2000, Cancer Res. 60: 3701-3705) (FIG. 1). The TR-PCR products were then subjected to adapter-PCR using adapter primers (Table 1) to create restriction sites at the 5'- and 3'-ends to facilitate further subcloning. The 200-300 bp adapter-PCR products (FIG. 1B) were eluted and cloned into the T-Easy vector (Promega). A clone containing 6 copies of the CETP epitope was identified by sequencing and subcloned into a modified plasmid pET21b vector (Novagen) at the 3'-end of the region coding for the Fc domain of the rabbit IgG. The resulting plasmid, pFc-CETP$_6$, was confirmed by sequencing and introduced into E. coli BL21 (DE3), and the expressed fusion protein (Fc-CETP$_6$) was purified by chromatography on a His-Bind column (Novagen).

TABLE 1

Primers used in construction

| Primer | Sequence |
|---|---|
| TR-PCR Forward | 5'-CCTGAACACCTGCTAGTTGATTTCCT CCAGAGCTTG-3' (SEQ ID NO: 8) |
| TR-PCR Reverse | 5'-AACTAGCAGGTGTTCGGACAAGCTCT GGAGGAAATC-3' (SEQ ID NO: 9) |
| AD-PCR Forward | 5'-GATCGGATCCCCTGAACACCTGCTAA GTT-3' (SEQ ID NO: 10) |
| AD-PCR Reverse | 5'-GATCGAATTCTAAAGCTTCAAGCTCT GGAGGAA-3' (SEQ ID NO: 11) |

Assay of Anti-CETP Antibody Titers

The GST and GST-CETP proteins were expressed in E. coli Top10 (Invitrogen), and purified by affinity chromatography. ELISA was applied using plates coated with GST-CETP or GST as tagging control to determine plasma antibody titers to CETP. The titer was defined as the plasma dilution that gave an optical density of 1.0 at 405 nm.

Animal Experiments

Two animal studies were conducted; in both, 16-week-old female New Zealand White rabbits (~2 kg) were allowed an adaptation period of 2 weeks, and then treated as follows.

In the first experiment, the rabbits were randomly allocated to the normal group (n=4), control group (n=7), or Fc-CETP$_6$ group (n=8). Rabbits in the normal group were fed a regular chow diet, while rabbits in the control and Fc-CETP$_6$ groups were fed the HFC diet (chow supplemented with 5% lard and 0.25% cholesterol). Each animal was fed 100 g of the diet per day during the study period and allowed open access to tap water. Rabbits in the Fc-CETP$_6$ group were injected subcutaneously with 0.1 mg of Fc-CETP$_6$ on day 1 and at the end of weeks 2, 4, 6, and 8 (first injection in complete Freund's adjuvant and all others in incomplete Freund's adjuvant), while the control HFC diet-fed group underwent the same schedule of injections with PBS in adjuvant. Plasma samples were collected at the end of weeks 1, 8, 12, 20, and 24 and CETP activity and titers of anti-CETP antibodies were measured. At week 24, the rabbits fasted overnight, and the next morning anesthetized by inhalation of isoflurane and the rabbits' aortas were also collected for atherosclerotic lesion analysis.

In the second experiment, the rabbits were treated as in the first experiment except that the Fc-CETP$_6$ group rabbits (n=8) received booster injections with 0.1 mg of Fc-CETP$_6$ in incomplete Freund's adjuvant at the end of weeks 24 and 28 and were sacrificed at the end of week 52. After overnight fasting, the rabbits were anesthetized as above and their liver removed after perfusion with physiological saline. Then three samples (each approximately 1 cm$^3$) of the right lobe were taken, fixed in 4% paraformaldehyde, and embedded in paraffin.

All procedures for the care and use of research animals were in accordance with the guidelines of, and approved by, the animal center of the Taiwan Food and Drug Administration, Department of Health, Executive Yuan.

Detection of CETP Activity

Plasma CETP activity was measured using CETP Activity Assay Kits (BioVision) according to the manufacturer's guidelines. The data are presented as a percentage of the levels before treatment.

Isolation of Lipoprotein Fractions and Measurement of Cholesterol Levels

The procedures used to isolate lipoprotein fractions have been described previously (Chang et al. 2004, J. Lipid Res. 45: 2116-2122). In brief, plasma was prepared by low speed centrifugation at 4° C., then VLDL, LDL, and HDL were isolated by density gradient ultracentrifugation and cholesterol concentrations in the plasma and lipoprotein fractions determined enzymatically (Randox) according to the manufacturer's guidelines.

Quantification of Atherosclerotic Lesions in the Aorta

The aorta was perfused for 20 min with ice-cold PBS, and then pressure-fixed with cold formaldehyde-sucrose solution (10% neutral formalin, 5% sucrose, 20 mM butylated hydroxytoluene, and 2 mM EDTA, pH 7.4). The entire aorta was then dissected out and the aorta opened longitudinally, rinsed briefly in 70% ethanol, and stained with Sudan IV (0.5% Sudan IV in 35% ethanol/50% acetone), and de-stained for 5 min with 80% ethanol. Each aorta was then mounted on a flat surface and images of its surface taken using a digital camera. The area stained with Sudan IV (lipid plaque) was expressed as a percentage of the total surface area of the aorta.

Immunohistochemical Analysis

The procedures used have been described previously (Chiang et al. 2012, Vaccine 30: 7573-7581). In brief, levels of NF-κB and RAM-1 expression in the aorta and liver tissue were determined by immunohistochemical staining using mouse anti-NF-κB and anti-RAM-11 antibodies (Dako). The aortas were analyzed from cross section from each animal and ten random fields (magnification, ×200) of each cross-section photographed under a microscope (Olympus, BX60). The liver tissues were analyzed from three tissue sections from right lobe of each animal and ten random fields (magnification, ×200) of each section photographed under a microscope (Olympus, BX60).

Liver Histology and Quantification of Steatosis and Fibrosis in the Liver

Liver sections (4 μm) were stained with hematoxylin and eosin (H&E) and Masson's trichrome stain. An expert pathologist assessed histological steatosis and fibrosis stages with the Histological Scoring System for Nonalcoholic Fatty Liver Disease (NAFLD) (Kleiner et al. 2005, Hepatology 41: 1313-1321). Three tissue sections from each animal were analyzed and ten random fields (magnification, ×200) of each section photographed under a microscope (Olympus, BX60).

Measurement of Plasma ApoA-I and Oxidized-LDL Levels

Plasma ApoA-I and plasma ox-LDL were measured using sandwich ELISA kits from CUSABIO (CSB-E09804Rb) and Mercodia (10-1158-01), respectively, according to the manufacturer's guidelines.

Statistical Analysis

All data are presented as the mean±SEM. Normality was examined by the Kolmogorov-Smirnov test, and when the data was normally distributed, the statistical significance of differences was assessed with the independent t test and 1-way ANOVA and by correlation and regression analysis using the SPSS statistical program, version 17. The Mann-Whitney U test was applied when the data was not normally distributed. In all analyses, values of P<0.05 were considered statistically significant.

Example 1. Generation of the Fc-CETP$_6$ Vaccine

Figure 1C:
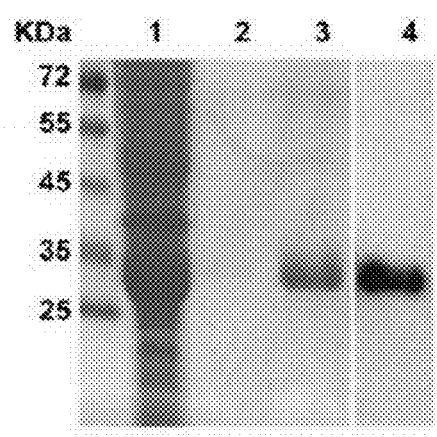

DNA encoding 6 repeats of CETP epitope was generated and the fusion protein was induced and expressed in E. coli strain BL21 (DE3) as shown in FIG. 1. The fusion protein Fc-CETP$_6$ was purified by affinity chromatography on a His-Bind column. The purity of the Fc-CETP$_6$ fusion protein examined by Coomassie Blue staining and Western blotting reached 95%. Purity of the His-Bind-purified Fc-CETP$_6$. Lanes 1 to 3 show Coomassie blue staining results for the flow-through fraction, wash fraction, and elutes, respectively, while lane 4 shows Western blot analysis of elutes using anti-rabbit IgG (Fc) antibodies (FIG. 1C).

Figure 2A:
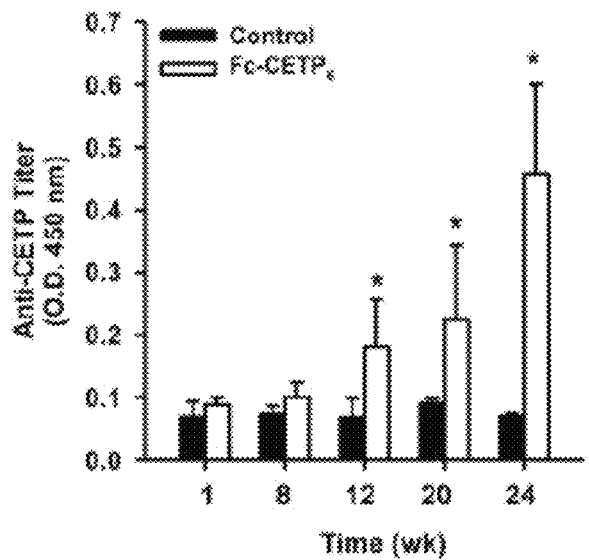
FIGS. 2A-B show the characterization of anti-CETP antibody in rabbits immunized with Fc-CETP6 (experiment 1).
Figure 2B:
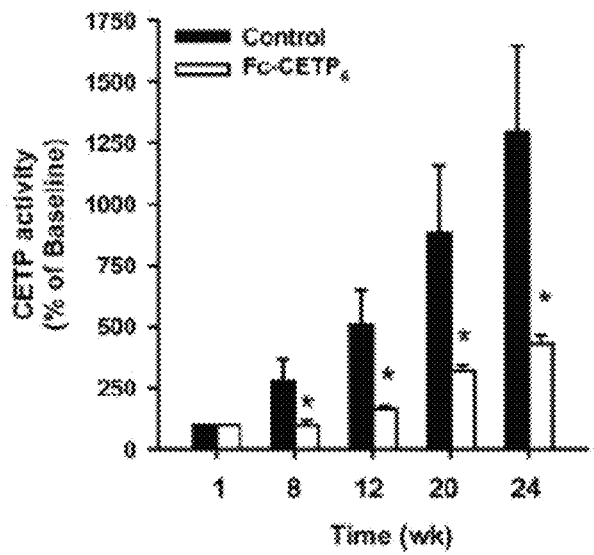

Example 2. Fc-CETP$_6$ Vaccine Elicits Antibodies Against CETP and Reduces CETP Activity in HFC Diet-Fed Rabbits To demonstrate that anti-CETP antibodies were produced and reacted with circulating CETP, the plasma anti-CETP titer and plasma CETP activity were measured. FIG. 2A shows that anti-CETP antibodies were detected in the Fc-CETP$_6$ group from week 12 and that the titer increased up until the end of the study at week 24. FIG. 2B shows that plasma CETP activity in both HFC diet-fed groups increased in a time-dependent manner, but was significantly lower in the Fc-CETP$_6$ group. These results show that injection of Fc-CETP$_6$ induces production of antibodies against CETP, which then reduce CETP activity.

Example 3. Effects of the Fc-CETP$_6$ Vaccine on Plasma Levels of Total-Cholesterol and HDL-Cholesterol The effects of vaccination with Fc-CETP$_6$ on levels of total-C and HDL-C and body weight are summarized in Table 2. There was no significant difference between the control and Fc-CETP$_6$ groups in body weight. Levels of total-C and HDL-C increased in a time-dependent manner in both groups. At weeks 12 and 24, total-C levels were significantly lower, and HDL-C levels significantly higher, in the Fc-CETP$_6$ group than in the control group. In addition, at weeks 12 and 24, the non-HDL-C/HDL-C ratio was lower in the Fc-CETP$_6$ group than in the control group. These results show that Fc-CETP$_6$ immunization resulted in a reduced atherogenic lipoprotein profile.

TABLE 2

Changes in body weight and plasma total cholesterol and HDL-C in rabbits fed the HFC diet with or without vaccination.

| Group | Time (week) | Body wt (kg) | Total C (mg dl$^{-1}$) | HDL-C (mg dl$^{-1}$) | Non-HDL-C/HDL-C |
|---|---|---|---|---|---|
| Control | 0 | 2.6 ± 0.1[1] | 127.0 ± 2.7 | 24.3 ± 3.7 | 4.5 ± 0.9 |
|  | 12 | 3.3 ± 0.3 | 342.7 ± 44.5 | 40.4 ± 5.4 | 7.5 ± 0.2 |
|  | 24 | 3.9 ± 0.3 | 454.6 ± 10.9 | 46.6 ± 7.2 | 8.8 ± 2.4 |
| Fc-CETP$_6$ | 0 | 2.5 ± 0.2 | 159.0 ± 19.9 | 29.8 ± 5.0 | 4.9 ± 1.0 |
|  | 12 | 3.2 ± 0.3 | 262.0 ± 18.8* | 52.8 ± 10.7* | 4.7 ± 0.9* |
|  | 24 | 3.4 ± 0.4 | 357.0 ± 11.2* | 54.5 ± 4.9* | 5.8 ± 0.7* |

Control n = 7; Fc-CETP$_6$ n = 8.
[1]Values are the mean ± SEM.
*p < 0.05 compared to the control at the same time

Example 4. Fc-CETP$_6$ Increases ApoA-I Levels and Lowers Ox-LDL Levels

ApoA-I is a major protein in HDL and is known to have anti-inflammatory effects (Navab et al. 2005, Trends Cardiovasc. Med. 15: 158-161); high levels of ApoA-I have been shown to reduce the progression and even induce regression of atherosclerosis, indicating that ApoA-I is directly protective against atherosclerosis (Smith JD 2010, Curr. Opin. Investig. Drugs 11: 989-996). In addition, ox-LDL is taken up by macrophages in the artery and transforms them into cholesterol-rich foam cells that have been shown to be involved in the development of NASH (Chalasani et al. 2004, Am. J. Gastroenterol. 99: 1497-1502). We therefore measured plasma levels of ApoA-I and ox-LDL in the rabbits (Table 3) and found that ApoA-I levels were significantly higher, and ox-LDL levels significantly lower, in the Fc-CETP$_6$ group than in the control group. In addition, the immunofluorescence stain showed the expression level of ox-LDL around the vein area of liver was significantly reduced in the Fc-CETP$_6$ group compared to control group (data not shown). These results may help explain why vaccination with Fc-CETP$_6$ alleviated development of HFC diet-induced atherosclerosis and NASH.

TABLE 3

Plasma levels of ApoA-I and ox-LDL.

| Plasma levels | Control | Fc-CETP$_6$ |
|---|---|---|
| ApoA-I (µg mL$^{-1}$) | 22.2 ± 7.5[1] | 96.2 ± 30.6* |
| ox-LDL (unit L$^{-1}$) | 61.6 ± 1.8 | 49.7 ± 5.2* |

Control n = 7; Fc-CETP$_6$ n = 8.
[1]Values are the mean ± SEM.
*p < 0.05 compared to control.

Figure 3A:
FIGS. 3A-E show the vaccination with Fc-CETP6 reduces aortic lesions and inflammation (experiment 1).
Figure 3B:
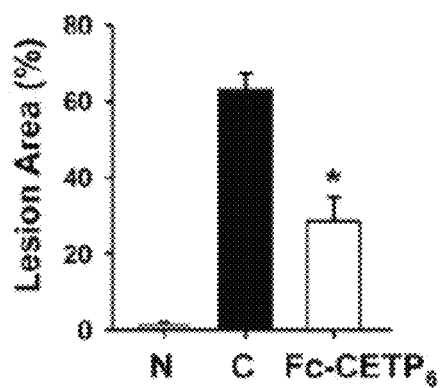
Figure 3C:
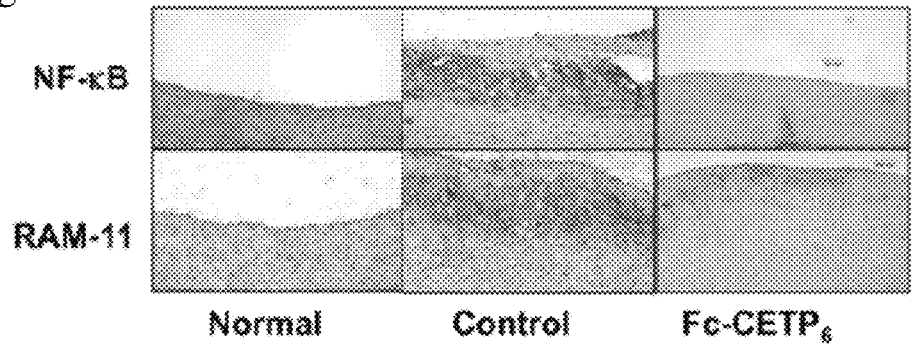
Figure 3D:
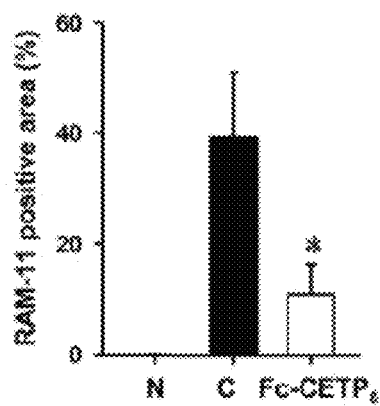
Figure 3E:
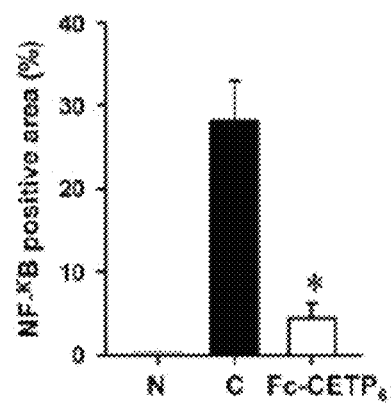

Example 5. Fc-CETP$_6$ Ameliorates HFC Diet-Induced Atherosclerotic Lesions and Inflammation in the Aorta To examine whether vaccination with Fc-CETP$_6$ could ameliorate formation of atherosclerotic plaques, the aorta from each rabbit was isolated and stained with Sudan IV. Representative Sudan IV-stained aorta from each group is shown in FIG. 3A, and the extent of atherosclerosis in the entire aorta, quantified using an image analysis system, is shown in FIG. 3B. In the normal rabbits, only about 1% of the aorta surface area stained by Sudan IV. In contrast, rabbits maintained on the HFC diet for 24 weeks developed atherosclerosis lesions that covered 62.9±4.3% of the aortic surface in the control group, but only 28.5±6.2% in the Fc-CETP6 group (FIG. 3B). Since atherogenesis involves long-term inflammation and the macrophage is considered a key mediator in aortic local inflammation (Libby P 2002, Nature 420: 868-874), an immunohistochemical analysis was performed to detect the presence of NF-κB, an inflammatory marker, and RAM-11, a macrophage marker, in the aorta. FIG. 3C shows that no NF-κB or RAM-11 staining was detected in the aorta of the normal rabbits, whereas the HFC diet resulted in strong RAM-11 and NF-κB staining in the intima in the control group. Both effects were significantly reduced by vaccination with Fc-CETP$_6$ (FIG. 3D) (FIG. 3E). In summary, our results show that immunization with Fc-CETP$_6$ reduced the extent of aortic inflammation and macrophage infiltration, and thus decreased susceptibility to atherosclerosis progression in the rabbit aorta.

Example 6. Fc-CETP$_6$ Alleviates HFC Diet-Induced NASH and Fibrosis

Figure 4A:
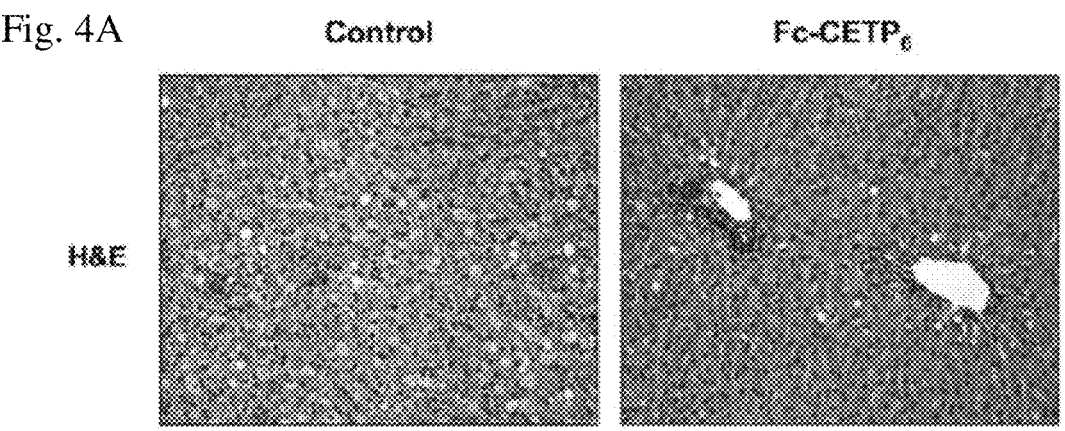
FIGS. 4A-E show the vaccination with Fc-CETP6 attenuates high HFC diet-induced steatosis and NASH.
Figure 4B:
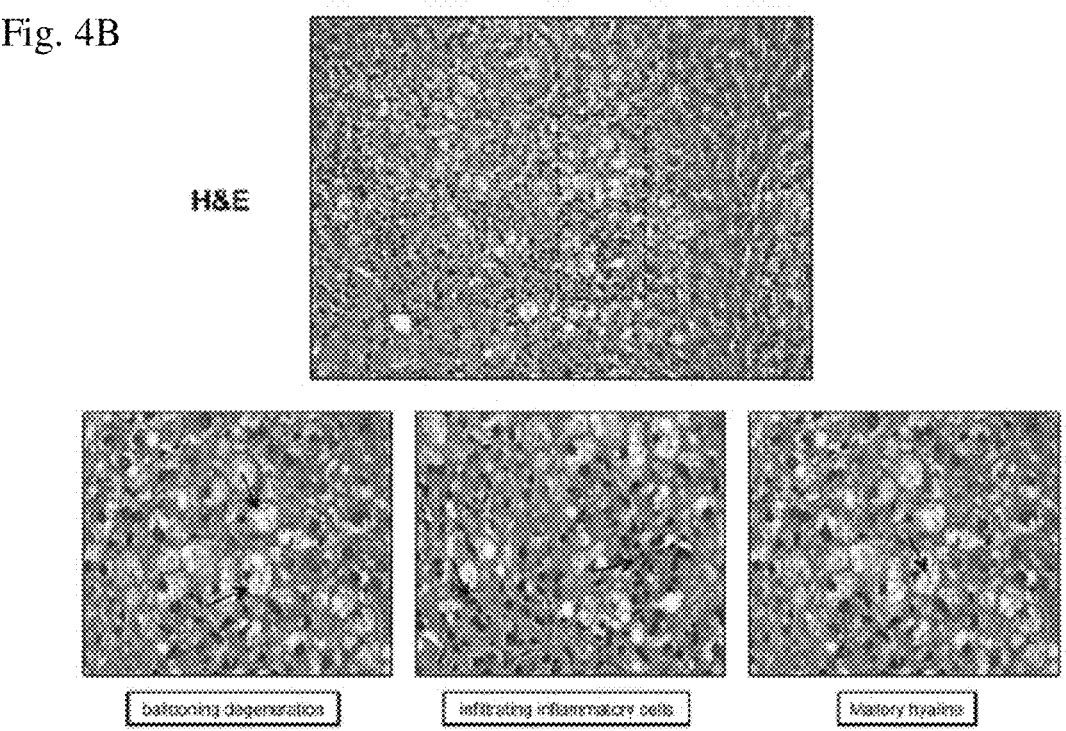
Figure 4C:
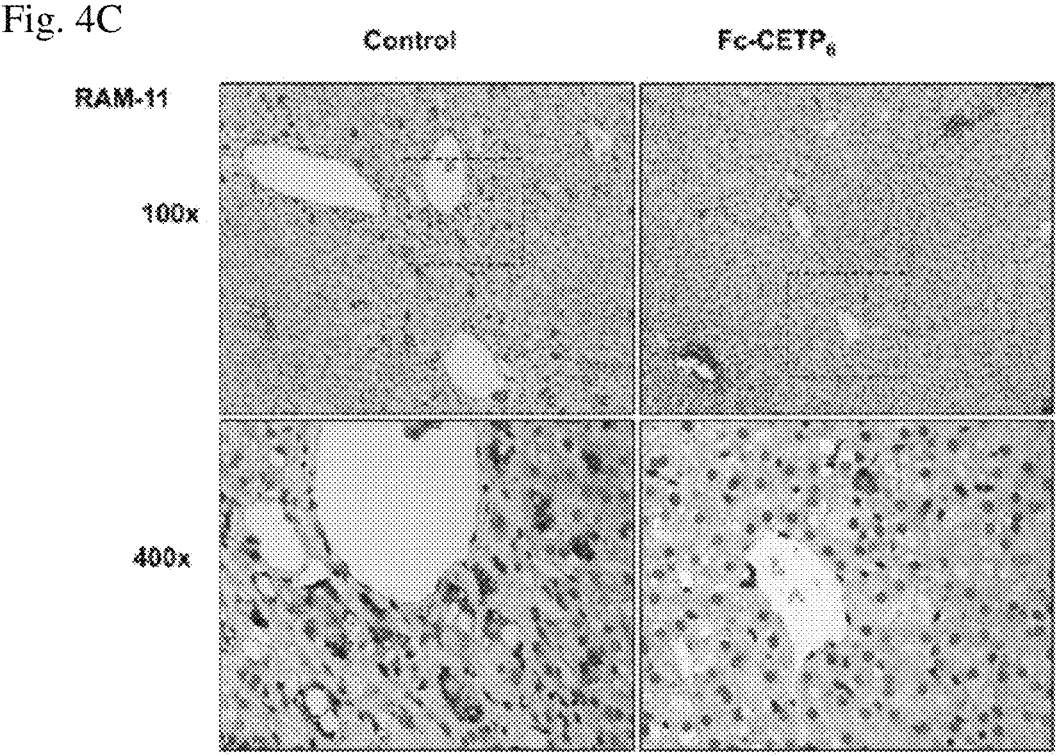
Figure 4D:
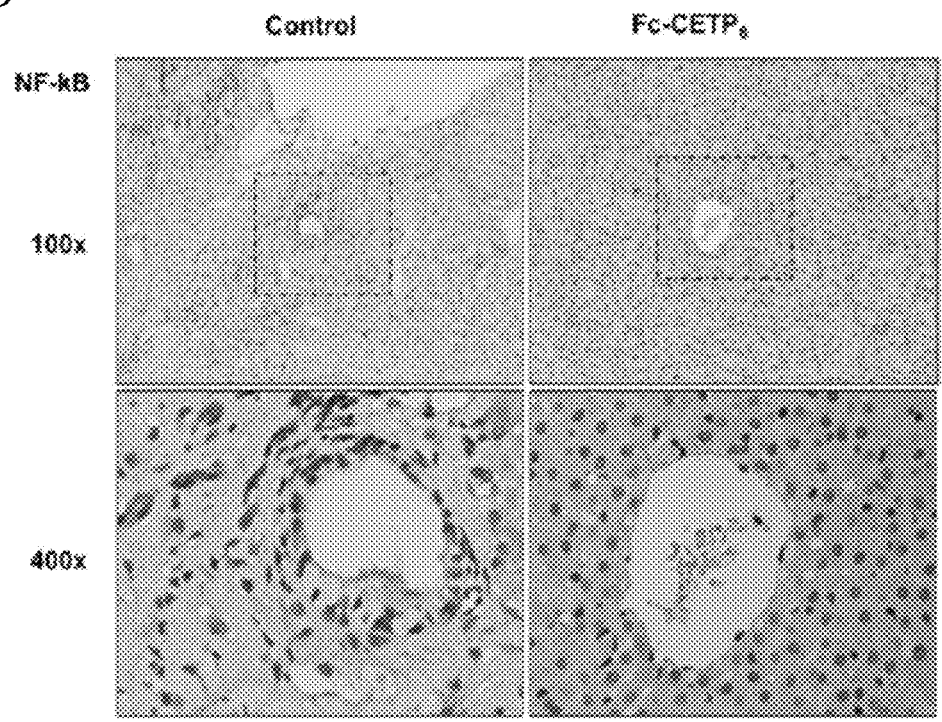
Figure 4E:
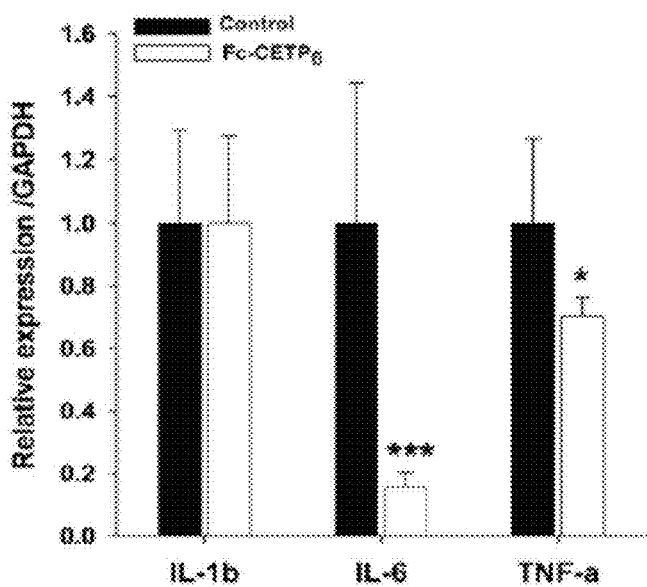

NASH is characterized by hepatic lipid accumulation combined with inflammation, which may ultimately progress into cirrhosis. In the first experiment designed to examine whether the vaccine was able to alleviate the atherosclerosis induced by the HFC diet, we observed that the livers from the control group were pale in color, while those from the normal group and Fc-CETP$_6$ group were red, suggesting that Fc-CETP$_6$ injection alleviated HFC-induced nonalcoholic fatty liver disease. Ogawa et al. found that a human-type NASH with advanced fibrosis is induced in rabbits by feeding a diet supplemented with 0.75% cholesterol and 12% corn oil (Ogawa et al. 2010, Am. J. Pathol. 177: 153-165). In the second experiment, to test whether the Fc-CETP$_6$ vaccine could reduce susceptibility to NASH and fibrosis in rabbits fed a HFC diet, we examined the effects of the Fc-CETP$_6$ vaccine on hepatic lipid accumulation and NASH in rabbits after 12 months of HFC diet feeding by staining of liver sections with H&E and Masson's trichrome. As shown in FIG. 4B, liver sections from the control group showed evidence of parenchymatous lipid accumulation, microvesicular steatosis with ballooning degeneration in the perivenular area, infiltrating inflammatory cells, and Mallory hyaline (FIG. 4B), whereas those from the Fc-CETP$_6$ group showed hepatocytes with only mild fat accumulation, and those from normal group showed no evidence of steatosis. To further evaluate the effects of Fc-CETP$_6$ on liver inflammation, immunohistochemistry staining was performed using antibodies against RAM-11, which recognizes activated kupffer cells (Buyssens et al. 1996, Hepatology 24: 939-946), and NF-κB, an inflammation marker. Compared to the liver of control rabbit, the liver of Fc-CETP$_6$ showed decreased number of RAM-11 positive cells around the central vein area at sites where fatty degeneration of hepatocytes was evident. Normal group was shown as RAM-11 negative control (FIG. 4C). At higher magnification, large RAM-11 positive cells contained vacuoles (lipid droplet). Moreover, NF-κB stained cells around central vein area in the liver of control rabbits, and NF-κB stained cells were significantly reduced in the Fc-CETP$_6$ group. Normal group was shown as NF-κB negative control (FIG. 4D). The changes of inflammation and fibrosis were further confirmed by detection of hepatic mRNA expression levels of pro-inflammatory cytokines and genes associated with fibrosis. FIG. 4E shows that mRNA levels of tumor necrosis factor alpha (TNFα) and interleukin-6 (IL-6) were significantly lower in the Fc-CETP$_6$ group than in the control group; whereas (interleukin 1β) IL-1β was not different between the two groups. These results support that Fc-CETP$_6$ reduces hepatic inflammation in the HFC diet fed rabbits.

Figure 5A:
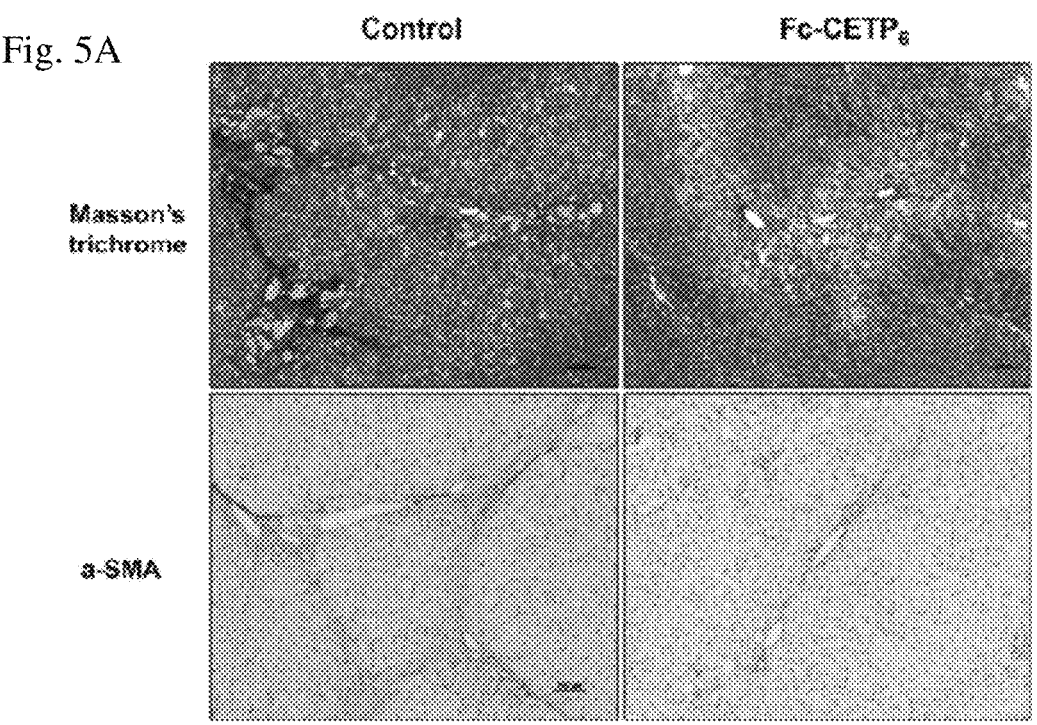
FIGS. 5A-B show that vaccination with Fc-CETP6 reduces inflammation related gene and fibrosis related gene expression profile (experiment 2).
Figure 5B:
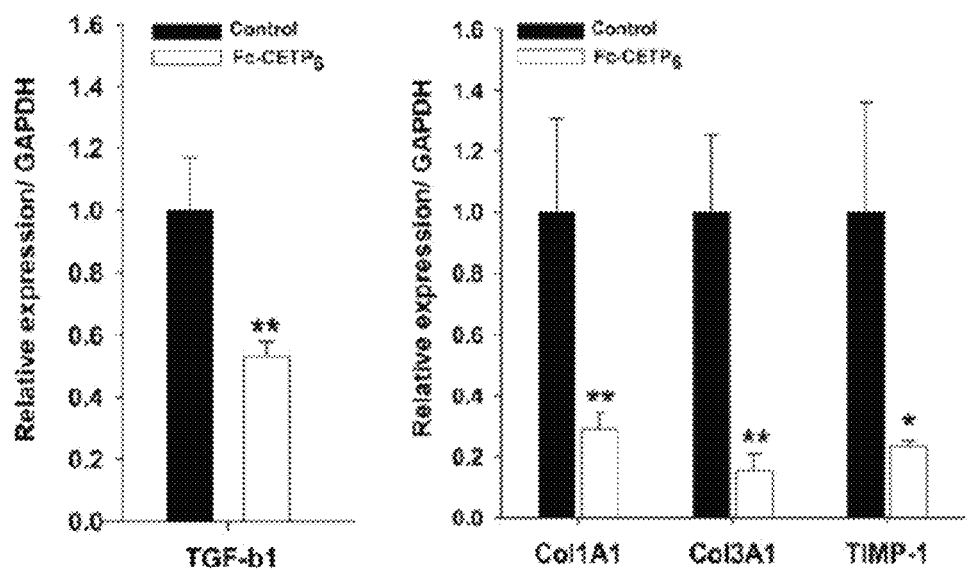

Liver sections from the control group showed positive trichrome staining, prominent bridging fibrosis with fibrous bands extending from the perivenular area to the pericellular area, whereas the Fc-CETP$_6$ group showed diminished, or no, bridging fibrosis. The fibrotic septa were composed of cells positive for α-SMA, a marker of activated stellate cells and myofibroblasts (FIG. 5A); whereas the Fc-CETP$_6$ group showed diminished bridging fibrosis that limited in central vein area. And hepatic mRNA levels of fibrosis associate genes, transforming growth factor β1 (TGF-β1), collagens 1A1 (CollA1), 3A1 (Col3A1) and tissue inhibitors of metalloproteinases-1 (TIMP-1) were all significantly lower in the liver of Fc-CETP$_6$ rabbits than in the liver of control rabbits (FIG. 5B). These results support that Fc-CETP$_6$ reduces hepatic fibrosis in the HFC diet fed rabbits.

The grades of steatosis and fibrosis are summarized in Table 4. In terms of steatosis, the results showed that, of the liver specimens from the control group, none were grade 0 or 1, 7% were grade 2, and 93% grade 3, whereas the values for the Fc-CETP$_6$ group were 12% grade 0, 56% grade 1, 32% grade 2, and none grade 3. In terms of fibrosis, in the control group, none were grade 0 or 1, while 25% were grade 2, 62.5% grade 3, and 12.5% grade 4, whereas in the Fc-CETP$_6$ group, 14% of the liver specimens presenting no fibrosis, while 29% were grade 1a, 43% grade 1b, 14% grade 2, and none grade 3 or 4 (see Table 4)

TABLE 4

Effects of the Fc-CETP6 vaccine on Hepatic Histology at 52 Weeks.

| Grading | Control | Fc-CETP$_6$ |
| --- | --- | --- |
| Steatosis(0-3)* | | |
| 0 | 0% | 12% |
| 1 | 0% | 56% |
| 2 | 7% | 32% |
| 3 | 93% | 0% |
| Fibrosis(0-4)† | | |
| 0 | 0% | 14% |
| 1a | 0% | 29% |
| 1b | 0% | 43% |
| 2 | 25% | 14% |
| 3 | 62.5% | 0% |
| 4 | 12.5% | 0% |

*Severity of hepatic steatosis is graded as: <5% (0); 5%-33% (1); 34%-66% (2); and >66% (3).
†Severity of hepatic fibrosis is graded as: none (0); perisinusoidal (1a); periportal (1b); periportal and perisinusoidal (2); bridging fibrosis (3); and cirrhosis (4).

What is claimed is:

1. An isolated antigenic peptide for eliciting a CETP antibody, comprising six repeats of an amino acid sequence consisting of PEHLLVDFLQSL (SEQ ID NO:1).

2. An antigenic fusion protein, comprising an antigenic peptide of claim 1 fused to a domain for increasing uptake by antigen presenting cells (APC).

3. The antigenic fusion protein of claim 2, wherein the domain for increasing uptake by antigen presenting cells (APC) is selected from the group including Fc fragment of IgG, Fc fragment of IgM, and Fc fragment of IgA.

4. The antigenic fusion protein of claim 2, wherein the domain is an Fc fragment of IgG.

5. The antigenic fusion protein of claim 2, which comprises the sequence encoded by SEQ ID NO:6 or SEQ ID NO:7.

6. A pharmaceutical agent or composition, comprising an isolated antigenic peptide of claim 1.

7. The pharmaceutical agent or composition of claim 6, which is a vaccine composition.

8. The pharmaceutical agent or composition of claim 6, which further comprises an adjuvant.

9. A method for eliciting or activating a CETP antibody in a subject, comprising administering an effective amount of an isolated antigenic peptide of claim 1 to the subject.

* * * * *

SEQUENCE LISTING

```
<160> NUMBER OF SEQ ID NOS: 11

<210> SEQ ID NO 1
<211> LENGTH: 12
<212> TYPE: PRT
<213> ORGANISM: Homo sapiens

<400> SEQUENCE: 1

Pro Glu His Leu Leu Val Asp Phe Leu Gln Ser Leu
1               5                   10

<210> SEQ ID NO 2
<211> LENGTH: 921
<212> TYPE: DNA
<213> ORGANISM: Homo sapiens

<400> SEQUENCE: 2
atggcacctg aactcctggg gggaccgtca gtcttcctct tcccccaaa  acccaaggac       60 accctcatga tctcccggac ccctgaggtc acatgcgtgg tggtggacgt gagccacgaa      120
gaccctgagg tcaagttcaa ctggtacgtg gacggcgtgg aggtgcataa tgccaagaca      180
aagccgcggg aggagcagta caacagcacg taccgtgtgg tcagcgtcct caccgtcctg      240
caccaggact ggctgaatgg caaggagtac aagtgcaagg tctccaacaa agccctccca      300
gcccccatcg agaaaaccat ctccaaagcc aaagggcagc ccgagaacc  acaggtgtac      360 accctgcccc catcccggga tgagctgacc aagaaccagg tcagcctgac ctgcctggtc      420
aaaggcttct atcccagcga catcgccgtg gagtgggaga gcaatgggca gccggagaac      480
aactacaaga ccacgcctcc cgtgctggac tccgacggct ccttcttcct ctacagcaag      540
```

-continued

```
ctcaccgtgg acaagagcag gtggcagcag gggaacgtct tctcatgctc cgtgatgcat      600
gaggctctgc acaaccacta cacgcagaag agcctctccc tgtctccggg taaaggatcc      660
ccttgttgtg gatgctgcgg ttgcggatgc ccttgttgtg gatgctgcgg ttgcggatgc      720
ccttgttgtg gatgctgcgg ttgcggatgc ccttgttgtg gatgctgcgg ttgcggatgc      780
ccttgttgtg gatgctgcgg ttgcggatgc ccttgttgtg gatgctgcgg ttgcggatgc      840
ccttgttgtg gatgctgcgg ttgcggatgc aagcttcatc accaccatca ccatgagctt      900
catcatcatc atcatcatta a                                                921
```

```
<210> SEQ ID NO 3
<211> LENGTH: 306
<212> TYPE: PRT
<213> ORGANISM: Homo sapiens

<400> SEQUENCE: 3
```

| Met | Ala | Pro | Glu | Leu | Gly | Gly | Pro | Ser | Val | Phe | Leu | Phe | Pro | Pro |
|---|---|---|---|---|---|---|---|---|---|---|---|---|---|---|
| 1 | | | | 5 | | | | | 10 | | | | | 15 |

| Lys | Pro | Lys | Asp | Thr | Leu | Met | Ile | Ser | Arg | Thr | Pro | Glu | Val | Thr | Cys |
|---|---|---|---|---|---|---|---|---|---|---|---|---|---|---|---|
| | | | 20 | | | | | 25 | | | | | 30 | | |

Val Val Val Asp Val Ser His Glu Asp Pro Glu Val Lys Phe Asn Trp
            35                  40                  45

Tyr Val Asp Gly Val Glu Val His Asn Ala Lys Thr Lys Pro Arg Glu
        50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys Gly Ser Pro Cys Cys Gly
    210                 215                 220

Cys Cys Gly Cys Gly Cys Pro Cys Cys Gly Cys Cys Gly Cys Gly Cys
225                 230                 235                 240

Pro Cys Cys Gly Cys Cys Gly Cys Gly Cys Pro Cys Cys Gly Cys Cys
                245                 250                 255

Gly Cys Gly Cys Pro Cys Cys Gly Cys Cys Gly Cys Gly Cys Pro Cys
            260                 265                 270

Cys Gly Cys Cys Gly Cys Gly Cys Pro Cys Cys Gly Cys Cys Gly Cys
        275                 280                 285

```
Gly Cys Lys Leu His His His His His Glu Leu His His His His
    290                 295                 300
His His
305

<210> SEQ ID NO 4
<211> LENGTH: 664
<212> TYPE: DNA
<213> ORGANISM: Oryctolagus cuniculus

<400> SEQUENCE: 4 gcccctcga caagcagcaa gcccacgtgc ccaccccctg aactcctggg gggaccgtct    60
gtcttcatct tccccccaaa acccaaggac accctcatga tctcacgcac ccccgaggtc   120
acatgcgtgg tggtggacgt gagccaggat gaccccgagg tgcagttcac atggtacata   180
aacaacgagc aggtgcgcac cgcccggccg ccgctacggg agcagcagtt caacagcacg   240
atccgcgtgg tcagcaccct ccccatcacg caccaggact ggctgagggg caaggagttc   300
aagtgcaaag tccacaaccg agaaaaccat ctccaaagcc agagggcagc ccctggagcc   360
gaaggtctac accatgggcc ctccccggga ggagctgagc agcaggtcgg tcagcctgac   420
ctgcatgatc aacggcttct acccttccga catctcggtg gagtgggaga gaacgggaa    480 ggcagaggac aactacaaga ccacgccggc cgtgctggac agcgacggct cctacttcct   540
ctacaacaag ctctcagtgc ccacgagtga gtggcagcgg ggcgacgtct tcacctgctc   600
cgtgatgcac gaggccttgc acaaccacta cacgcagaag tccatctccc gctctccggg   660
taaa                                                                664

<210> SEQ ID NO 5
<211> LENGTH: 322
<212> TYPE: PRT
<213> ORGANISM: Oryctolagus cuniculus

<400> SEQUENCE: 5

Ala Pro Ser Thr Ser Ser Lys Pro Thr Cys Pro Pro Pro Glu Leu Leu
1               5                   10                  15

Gly Gly Pro Ser Val Phe Ile Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Asp Asp Pro Glu Val Gln Phe Thr Trp Tyr Ile Asn Asn Glu Gln
    50                  55                  60

Val Arg Thr Ala Arg Pro Pro Leu Arg Glu Gln Gln Phe Asn Ser Thr
65                  70                  75                  80

Ile Arg Val Val Ser Thr Leu Pro Ile Thr His Gln Asp Trp Leu Arg
                85                  90                  95

Gly Lys Glu Phe Lys Cys Lys Val His Asn Lys Ala Leu Pro Ala Pro
            100                 105                 110

Ile Glu Lys Thr Ile Ser Lys Ala Arg Gly Gln Pro Leu Glu Pro Lys
        115                 120                 125

Val Tyr Thr Met Gly Pro Pro Arg Glu Glu Leu Ser Ser Arg Ser Val
    130                 135                 140

Ser Leu Thr Cys Met Ile Asn Gly Phe Tyr Pro Ser Asp Ile Ser Val
145                 150                 155                 160

Glu Trp Glu Lys Asn Gly Lys Ala Glu Asp Asn Tyr Lys Thr Thr Pro
                165                 170                 175
```

Ala Val Leu Asp Ser Asp Gly Ser Tyr Phe Leu Tyr Asn Lys Leu Ser
            180                 185                 190

Val Pro Thr Ser Glu Trp Gln Arg Gly Asp Val Phe Thr Cys Ser Val
            195                 200                 205

Met His Glu Ala Leu His Asn His Tyr Thr Gln Lys Ser Ile Ser Arg
    210                 215                 220

Ser Pro Gly Lys Gly Ser Pro Cys Cys Gly Cys Cys Gly Cys Gly Cys
225                 230                 235                 240

Pro Cys Cys Gly Cys Cys Gly Cys Gly Cys Pro Cys Cys Gly Cys Cys
                245                 250                 255

Gly Cys Gly Cys Pro Cys Cys Gly Cys Cys Gly Cys Gly Cys Pro Cys
            260                 265                 270

Cys Gly Cys Cys Gly Cys Gly Cys Pro Cys Cys Gly Cys Cys Gly Cys
                275                 280                 285

Gly Cys Pro Cys Cys Gly Cys Cys Gly Cys Gly Cys Lys Leu Arg Ser
            290                 295                 300

Gly His His His His His His Gly Arg Ser Gly His His His His His
305                 310                 315                 320

His Gly

<210> SEQ ID NO 6
<211> LENGTH: 948
<212> TYPE: DNA
<213> ORGANISM: Artificial Sequence
<220> FEATURE:
<223> OTHER INFORMATION: hFc-CETP6

<400> SEQUENCE: 6

```
catatggcac ctgaactcct ggggggaccg tcagtcttcc tcttcccccc aaaacccaag    60
gacaccctca tgatctcccg gacccctgag gtcacatgcg tggtggtgga cgtgagccac   120
gaagaccctg aggtcaagtt caactggtac gtggacggcg tggaggtgca taatgccaag   180
acaaagccgc gggaggagca gtacaacagc acgtaccgtg tggtcagcgt cctcaccgtc   240
ctgcaccagg actggctgaa tggcaaggag tacaagtgca aggtctccaa caaagccctc   300
ccagccccca tcgagaaaac catctccaaa gccaagggc agccccgaga accacaggtg   360
tacaccctgc ccccatcccg ggatgagctg accaagaacc aggtcagcct gacctgcctg   420
gtcaaaggct tctatcccag cgacatcgcc gtggagtggg agagcaatgg gcagccggag   480
aacaactaca agaccacgcc tcccgtgctg gactccgacg gctccttctt cctctacagc   540
aagctcaccg tggacaagag caggtggcag caggggaacg tcttctcatg ctccgtgatg   600
catgaggctc tgcacaacca ctacacgcag aagagcctct ccctgtctcc gggtaaagga   660
tccccttgtt gtggatgctg cggttgcgga tgcccttgtt gtggatgctg cggttgcgga   720
tgcccttgtt gtggatgctg cggttgcgga tgcccttgtt gtggatgctg cggttgcgga   780
tgcccttgtt gtggatgctg cggttgcgga tgcccttgtt gtggatgctg cggttgcgga   840
tgcccttgtt gtggatgctg cggttgcgga tgcaagctta gatcaggtca tcatcaccac   900
catcacggta gatcaggtca tcatcaccac catcacggtt aagaattc                948
```

<210> SEQ ID NO 7
<211> LENGTH: 981
<212> TYPE: DNA
<213> ORGANISM: Artificial Sequence
<220> FEATURE:
<223> OTHER INFORMATION: rFc-CETP6

<400> SEQUENCE: 7

```
catatggccc cctcgacaag cagcaagccc acgtgcccac cccctgaact cctgggggga    60
ccgtctgtct tcatcttccc cccaaaaccc aaggacaccc tcatgatctc acgcacccccc   120
gaggtcacat gcgtggtggt ggacgtgagc caggatgacc ccgaggtgca gttcacatgg   180
tacataaaca cgagcaggt gcgcaccgcc cggccgccgc tacgggagca gcagttcaac    240
agcacgatcc gcgtggtcag caccctcccc atcacgcacc aggactggct gaggggcaag   300
gagttcaagt gcaaagtcca caacaaggca ctcccggccc ccatcgagaa aaccatctcc   360
aaagccagag ggcagcccct ggagccgaag gtctacacca tgggccctcc ccggaggag    420
ctgagcagca ggtcggtcag cctgacctgc atgatcaacg gcttctaccc ttccgacatc   480
tcggtggagt gggagaagaa cgggaaggca gaggacaact acaagaccac gccggccgtg   540
ctggacagcg acggctccta cttcctctac aacaagctct cagtgcccac gagtgagtgg   600
cagcggggcg acgtcttcac ctgctccgtg atgcacgagg ccttgcacaa ccactacacg   660
cagaagtcca tctcccgctc tccgggtaaa ggatccccct tgttgtggatg ctgcggttgc   720
ggatgccctt gttgtggatg ctgcggttgc ggatgccctt gttgtggatg ctgcggttgc   780
ggatgccctt gttgtggatg ctgcggttgc ggatgccctt gttgtggatg ctgcggttgc   840
ggatgccctt gttgtggatg ctgcggttgc ggatgccctt gttgtggatg ctgcggttgc   900
ggatgcaagc ttagatcagg tcatcatcac caccatcacg gtagatcagg tcatcatcac   960
caccatcacg gttaagaatt c                                             981
```

<210> SEQ ID NO 8
<211> LENGTH: 36
<212> TYPE: DNA
<213> ORGANISM: Artificial Sequence
<220> FEATURE:
<223> OTHER INFORMATION: TR-PCR Forward

<400> SEQUENCE: 8

```
cctgaacacc tgctagttga tttcctccag agcttg                              36
```

<210> SEQ ID NO 9
<211> LENGTH: 36
<212> TYPE: DNA
<213> ORGANISM: Artificial Sequence
<220> FEATURE:
<223> OTHER INFORMATION: TR-PCR Reverse

<400> SEQUENCE: 9

```
aactagcagg tgttcggaca agctctggag gaaatc                              36
```

<210> SEQ ID NO 10
<211> LENGTH: 29
<212> TYPE: DNA
<213> ORGANISM: Artificial Sequence
<220> FEATURE:
<223> OTHER INFORMATION: AD-PCR Forward

<400> SEQUENCE: 10

```
gatcggatcc cctgaacacc tgctaagtt                                      29
```

<210> SEQ ID NO 11
<211> LENGTH: 33
<212> TYPE: DNA
<213> ORGANISM: Artificial Sequence

```
<220> FEATURE:
<223> OTHER INFORMATION: AD-PCR Reverse

<400> SEQUENCE: 11
gatcgaattc taaagcttca agctctggag gaa                                    33
```